United States Patent [19]

McManus

[11] Patent Number: 5,550,288
[45] Date of Patent: Aug. 27, 1996

[54] PROCESS FOR THE PREPARATION OF α-AMINOACYLANILIDES

[75] Inventor: James W. McManus, Leesburg, Ga.

[73] Assignee: Merck & Co., Inc., Rahway, N.J.

[21] Appl. No.: 335,806

[22] PCT Filed: Jun. 11, 1993

[86] PCT No.: PCT/US93/05613

§ 371 Date: Nov. 14, 1994

§ 102(e) Date: Nov. 14, 1994

[87] PCT Pub. No.: WO93/25518

PCT Pub. Date: Dec. 23, 1993

[51] Int. Cl.$^6$ .................. C07C 235/68; C07C 237/06
[52] U.S. Cl. .................................................. 564/194
[58] Field of Search .................. 564/194; 560/14

[56] References Cited

U.S. PATENT DOCUMENTS

| | | | |
|---|---|---|---|
| 2,851,494 | 9/1958 | Ehrhart et al. | 564/194 |
| 3,210,412 | 10/1965 | Chapman | 562/442 |
| 4,169,106 | 9/1979 | Diamond et al. | 564/157 |
| 4,218,477 | 8/1980 | Boyes et al. | 424/324 |

FOREIGN PATENT DOCUMENTS

| | | |
|---|---|---|
| 63-39844 | 2/1988 | Japan . |
| 1374367 | 11/1974 | United Kingdom . |
| 1420067 | 1/1976 | United Kingdom . |
| 1461602 | 1/1977 | United Kingdom . |
| WO91/12265 | 8/1991 | WIPO . |

OTHER PUBLICATIONS

"New Antiarrhythmic Agents. 1. Primary alpha–Amino Anilides", Eugene W. Byrnes, et al., Journal of Medicinal Chemistry, 1979, vol. 22, No. 10, pp. 1171–1176.

"New Antiarrhythmic Agents. 2. Amide Alkyl alpha–Amino Xylidides", Paul D. McMaster, et al., Journal of Medicinal Chemistry, 1979, vol. 22, No. 10, pp. 1177–1182.

The Merck Index, 10th Edition, Compound No. 518, p. 76 (1988).

*Primary Examiner*—Shailendra Kumar
*Attorney, Agent, or Firm*—Robert J. North; Melvin Winokur

[57] ABSTRACT

A novel process for the preparation of α-aminoacylanilides comprises the treatment of the corresponding α-haloacylanilides with a solution of ammonium carbamate in aqueous ammonia. The process is especially useful in the preparation of certain active cardiac antiarrhythmic agents, such as tocainide.

4 Claims, No Drawings

PROCESS FOR THE PREPARATION OF α-AMINOACYLANILIDES

This application is a 371 of PCT/US93/05613 filed Jun. 11, 1993.

BACKGROUND OF THE INVENTION

Compounds of the general Formula I have been described as effective long lasting cardiac antiarrhythmic agents.

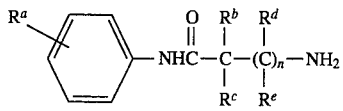

Of particular interest are the compounds of Formula I wherein variable n is zero, compounds generally described as α-aminoacylanilides. Tocainide, an example of an α-aminoacylanilide, is a commercially marketed antiarrhythmic agent.

Synthetic preparations of compounds of the Formula I wherein n is zero have been previously described (see for example U.S. Pat. No. 4,218,477).

Of the known synthetic routes the preferred preparation of the α-aminoacylanilides comprises synthesis of the suitably substituted α-haloacylanilide followed by reaction of the haloacylanilide and ammonia gas in a suitable organic/aqueous solvent. The reaction of the haloacylanilide typically proceeds in high yield; however, because the terminal nitrogen of the product, α-aminoacylanilide, is comparable in nucleophilicity to ammonia, a byproduct of the Formula II may form in amounts which are unacceptable for pharmaceutical applications.

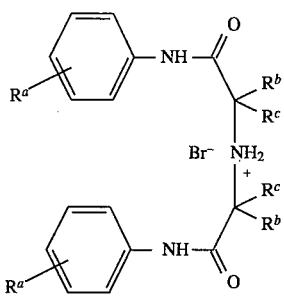

Small amounts of byproducts of the Formula II may be removed, or reduced to be within acceptable pharmaceutical limits, by recrystallization of the reaction product or washing the reaction product with a suitable organic solvent. However, this additional step presents added economic costs and the potential utilization of environmentally harmful solvents.

An alternative amination procedure utilizes aqueous ammonia in high dilution without an organic cosolvent. While the amount of the above described byproduct is reduced under this reaction condition, it is still present in such amounts as to require further purification as previously described. This second procedure is also unacceptable because of the enormous size of the vessels which would be required for implementation on a manufacturing scale. Thus, there now exists a need for a simple, economic procedure for preparing α-aminoacylanilides from α-haloacylanilides wherein the dimeric byproduct of the reaction is substantially reduced or eliminated.

It is an object of the instant invention to provide an improved process for the preparation α-aminoacylanilides by amination of the corresponding α-haloacylanilides with a solution of ammonium carbamate in aqueous ammonia. It has been surprisingly discovered that under these conditions the unwanted dimer byproduct has been essentially eliminated from the crude reaction product.

The α-aminoacylanilide compound of Formula I produced by the process of the present invention is useful per se as an antiarrhythmic agent, such as disclosed in U.S. Pat. No. 4,218,477. It is also understood that the compound of Formula I may be further modified and that such modification may lead to other pharmaceutical agents, such as disclosed in U.S. Pat. No. 4,169,106 and PCT application WO 91/12265.

SUMMARY OF THE INVENTION

The present invention provides a novel process for the preparation of a compound of the Formula I:

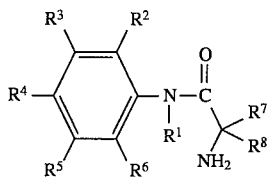

wherein:
$R^1$ is H lower alkyl or aryl;
   wherein aryl is phenyl or substituted phenyl with one or two substituents selected from the group consisting of Cl, Br, I, F, $NH_2$, —NH—(lower alkyl), —N(lower alkyl)$_2$, $CO_2H$, —$CO_2$—(lower alkyl), lower alkoxy, $NO_2$, $CF_3$, lower alkylthio or OH;
$R^2$, $R^3$, $R^4$, $R^5$ and $R^6$ are each independently selected from: H, lower alkyl, lower alkoxy, Cl, Br, I and F; and
$R^7$ and $R^8$ are independently selected from: H and lower alkyl;
WHICH COMPRISES treating the acylanilide of the Formula III

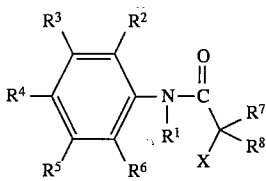

wherein $R^1$, $R^2$, $R^3$, $R^4$, $R^5$, $R^6$, $R^7$ and $R^8$ are as defined hereinabove; and X is Cl, Br, I, p-toluenesulfonyloxy, trifluoromethyl sulfonyloxy or methylsulfonyloxy;

WITH A MIXTURE OF ammonium carbamate and aqueous ammonia solution, at a temperature from 40° to 80° C.

One embodiment of the process of the instant invention is that process in which the molar ratio of ammonium carbamate to the acylanilide of the Formula III is selected from a range of 3.0/1 to 3.5/1 and the molar ratio of ammonia in the aqueous ammonia to the acylanilide of the Formula III is selected from a range of 12/1 to 15/1.

One class of this embodiment is the process wherein the temperature is from 55° to 70° C.

Another embodiment of the process of the instant invention is that process for the preparation of a compound of the Formula Ia, tocainide:

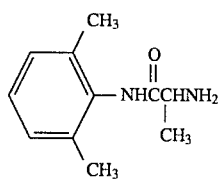

which comprises treating the acylanilide of the Formula IIIa

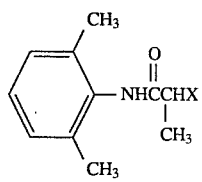

wherein X is Cl, Br or I; with a mixture of ammonium carbamate and aqueous ammonia solution, at a temperature from 40° to 80° C.

Definitions

The following abbreviations have the indicated meanings:
Me=methyl
Bz=benzyl
Ph=phenyl
t-Bu=tert-butyl
i-Pr=isopropyl
c-C$_6$H$_{11}$=cyclohexyl
Ac=acetyl Alkyl is intended to include linear, branched, and cyclic structures and combinations thereof.

As used herein, the term "alkyl" includes "lower alkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-diethyl-2,2-dimethyl-4-propylnonyl, cyclododecyl, adamantyl, and the like.

As used herein, the term "lower alkyl" includes those alkyl groups of from 1 to 7 carbon atoms. Examples of lower alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like. The preferred lower alkyl groups are methyl, ethyl, propyl and butyl.

As used herein, the term "lower alkoxy" includes those alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

As used herein, the term "lower alkylthio" includes those alkylthio groups of from 1 to 7 carbon atoms of a straight, branched or cyclic configuration. Examples of lower alkylthio groups include methylthio, propylthio, isopropylthio, cycloheptylthio, etc. By way of illustration, the propylthio group signifies —SCH$_2$CH$_2$CH$_3$.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

DETAILED DESCRIPTION OF THE INVENTION

The following synthetic schemes illustrate reaction sequences in which the process of the instant invention is employed.

Synthetic Scheme 1 illustrates generally the sequence in which the process of the instant invention is employed. The various substituents and variables $R^1$, $R^2$, $R^3$, $R^4$, $R^5$, $R^6$, $R^7$, $R^8$ are defined hereinabove.

It will be apparent to one skilled in the art that the various substituents and functional groups ($R^1$, $R^2 R^3$ $R^4$ etc.) must be chosen so as to be compatible with the chemistry being carried out. Such compatibility can often be achieved by protecting groups, or by specific variations in the sequence of the reactions.

Scheme 1

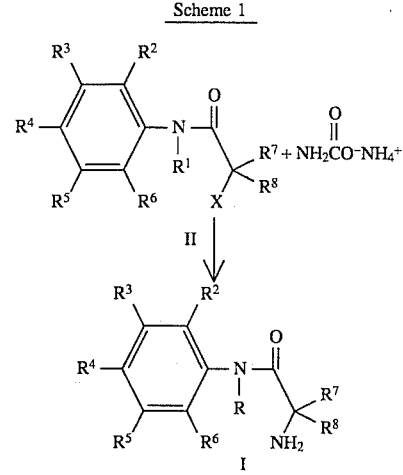

The steps for preparing the substituted acylanilide II are well known in the art (see for example U.S. Pat. Nos. 4,169,106 and 4,218,477; and *J. Med. Chem.*, 22, 1171 and 1177 (1979)).

In words relative to the equations, the substituted acylanilide II is reacted with ammonium carbamate in the presence of aqueous ammonia solution for a period of time and at a temperature sufficient to produce the α-aminoacylanilide I. Subsequent isolation may be carried out which takes advantage of the basic character of the α-amino moiety. The product α-aminoacylanilide may be further purified by recrystallization or washing with a suitable solvent.

Scheme 2 illustrates a sequence in which the process of the instant invention is employed in the synthesis of tocainide, a known antiarrhythmic agent. This scheme is illustrative and is not meant to be limiting.

Scheme 2

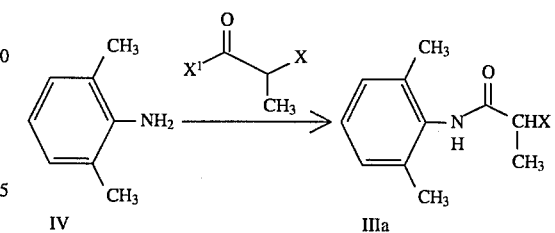

-continued
Scheme 2

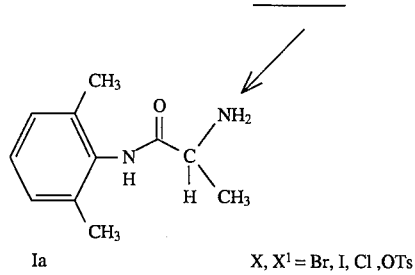

Ia  X, X¹ = Br, I, Cl, OTs

The 2,6-dimethyl aniline starting material IV is commercially available.

In words relative to the equation of Scheme 2 xylidine (2,6-dimethylaniline) is treated with a suitably substituted propionyl reagent, such as 2-bromopropionylbromide, 2-chloro-propionylchloride, 2-bromopropionylchloride and the like, in the presence of a suitable base, such as sodium carbonate, sodium bicarbonate, and the like, and, optionally, in the presence of a suitable catalyst, such as sodium sulfite, and the like, in a suitable solvent, such as toluene-water mixture, tetrahydrofuran-water mixture and the like, at a temperature and for a period of time sufficient to produce the suitably activated acyl anilide IIIa. Appropriate reaction workup then provided the isolated acylanilide IIIa.

The acylanilide IIIa is treated with a solution of ammonium carbamate in aqueous ammonia at a temperature and for a period of time sufficient to produce tocainide I. The product is subsequently isolated as either the free base or as a suitable pharmaceutically acceptable salt, such as the hydrochloride salt and the like.

The following examples illustrate the process of the instant invention but are not meant to be limiting.

EXAMPLE 1

Preparation of 2-bromo-2', 6'-propionoxylidide

To a 1L round bottom flask fitted with an overhead stirrer, thermometer, condenser, and dropping funnel was added sodium carbonate (28.1 g, 0.265 moles), sodium sulfite (0.353 g, 2.8 mmol) and 136 mL of water. The mixture was then stirred until complete dissolution of the inorganic salts. To this solution, xylidine (53 g, 0.437 moles) and 104 mL of toluene were added and the mixture was heated to 50°–55° C. Bromopropionyl bromide (BPB) (50.4 mL, 0.459 moles) was then added over a 2.5 hour time period while maintaining a temperature of 57° C. or less. The addition funnel was rinsed forward with 5 mL toluene.

Following the addition, toluene was removed by atmospheric distillation until a vapor temperature of 100° C. was obtained (approximately 112 mL of distillate was collected, 98 mL of toluene and 12 mL water).

After the toluene was removed, the batch was cooled to 25°–30° C. and the mother liquor separated by pressure filtration, in situ, through a glass tube terminating with a course, sintered glass plate. Approximately 80 mL of mother liquor was obtained.

Approximately 350 mL water was then added to the solid bromoamide and the batch agitated vigorously for fifteen minutes to insure complete dissolution of all unconverted xylidine and excess BPB. The slurry was transferred to a 1L autoclave and flushed forward with 50 mL additional water. The wash was removed by pressure filtration, in situ, as above.

EXAMPLE 2

Preparation of 2-amino-2', 6'-propionoxylidide hydrochloride

Method A: Amination with Ammonium Carbamate in Aqueous Ammonia

To a 1L stainless steel autoclave was added 2-bromo-2', 6'-propionoxylidide (105.5 g, 0.412 mol) (prepared as described in Example 1) and a solution of ammonium carbamate (110 gm, 1.41 mol) in 360 mL of concentrated ammonia water. The reactor was sealed and with vigorous agitation the mixture was heated to 60° C. to 65° C. and aged for 10 hours. Following the age the mixture was concentrated by atmospheric distillation to ca. 200 mL. The resulting solution was cooled to 70° C. to 75° C., the pH adjusted to 10.5 to 10.8 with 50% sodium hydroxide and the 2-amino-2', 6'-propionoxylidide free-base extracted with 2×150 mL hot toluene (70°14 75° C.).

The organic layers were combined and diluted to 600 mL with toluene. Anhydrous HCl (15.9 gm) was then added subsurfacely, over a four-hour period, while maintaining a temperature of 25° C. to 30° C. Following HCl1 addition, the batch was aged at 20° C. to 25° C. for one hour, then filtered, washed with 25 mL toluene and dried (50 mm Hg, 90° C. to 100° C.). Yield 93.2 g (99%); the product showed single peak by analytical HPLC; m.p. 247° C.–248° C.; ¹H NMR (400 MHz, DMSO-d₆) δ 8.34 (s, 1H), 7.08 (m, 3H), 4.14 (q, 1H), 2.19 (s, 6H), 1.52 (d, 3H).

Method B: Amination with Ammonium Carbonate in Aqueous Ammonia

To a 1L autoclave containing the 2-bromo-2', 6'-propionoxylidide (64 g, 0.25 moles) prepared as described in Example 1 was added 358 mL (5.01 moles) of aqueous ammonia and 80.5 g of ammonium carbonate. The reaction mixture was vigorously agitated for 2 hours at 65° C., then allowed to cool and filtered through a filter aid. The crude filtrate was analyzed by analytical HPLC which showed that 2.3% of the reaction product was the dimer biproduct of the Formula IIa.

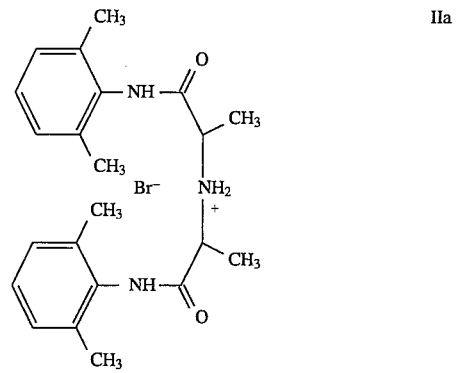

IIa

Method C: Amination with Aaueous Ammonia

To a 1L autoclave containing the 2-bromo-2', 6'-propionoxylidide (63.7 g, 0.25 moles), prepared as described in Example 1, was added 358 mL (5.01 moles) of aqueous ammonia. The reaction mixture was vigorously agitated for 12.5 hours in the sealed autoclave (36 to 31 psig) then the reaction mixture was allowed to cool. The mixture was then filtered through a filter aid and the crude liltrate was analyzed by analytical HPLC which showed that 2.9% of the reaction product was the dimer biproduct of the Formula IIa.

The following compounds were prepared utilizing the procedures described in Example 1 and Example 2, Method A, but substituting the appropriate substituted aniline compound for the xylidine employed in Example 1.

EXAMPLE 3

Preparation of 2-Amino-2', 6'-Diethylpropionylanilide Hydrochloride

Following the procedure described for Example 2, 2-bromo-2', 6'-Diethylpropionylanilide (66.1 gm, 0.232 mol) yielded 58.9 g (99.2%) of the title compound. Product showed single peak by analytical HPLC; m.p. 247° C.–248° C.; $^1$H NMR (400 MHz, DMSO-$d_6$) δ 8.28 (s, 1H), 7.15 (m, 3H), 4.14 (q, 1H), 1.53 (d, 3H) 1.09 (5, 6H).

EXAMPLE 4

Preparation of 2-Amino-2', 6'-Dichloropropionylanilide Hydrochloride

Following the procedure described for Example 2, 2-bromo-2', 6'-Dichloropropionylanilide (69.2 gm, 0.233 mol) yielded 61.9 g (99.1%) of the title compound. Product showed single peak by analytical HPLC; m.p. 256° C.–258° C.; $^1$H NMR (400 MHz, DMSO-$d_6$) δ 8.42 (s, 1H), 7.58 (m, 3H), 4.14 (q, 1H), 1.56 (d, 3H).

EXAMPLE 5

Preparation of 2-Amino-2'-Methoxypropionylanilide Hydrochloride

Following the procedure described for Example 2, 2-bromo-2'-methoxypropionylanilide (57.8 gm, 0.231 mol) yielded 52.5 gm (98.8%) of the title compound.

Product showed a single peak by analytical HPLC; m.p. 120° C.–121° C.; $^1$H NMR (400 MHz, DMSO-$d_6$) δ 8.35 (s, 1H), 7.40 (m, 4H), 4.18 (q, 1H), 3.82 (s, 3H), 1.43 (d, 3H).

EXAMPLE 6

Preparation of 2-Amino-Propionylanilide Hydrochloride

Following the procedure described for Example 2, 2-bromo-N-phenylpropionamide (5 gm, 0.022 mol) yielded 4.36 gm (99%) of the title compound. Product showed a single peak by analytical HPLC; m.p. 176° C.–178° C.; $^1$H NMR (400 MHz, DMSO-$d_6$) δ 8.35 (s, 1H), 7.36 (m, 5H), 4.09 (q, 1H), 1.46 (d, 3H).

What is claimed is:

1. A process for the preparation of a compound of the Formula I:

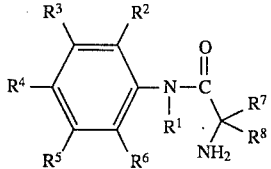

I wherein:

$R^1$ is H, lower alkyl or aryl;

wherein aryl is phenyl or substituted phenyl with one or two substituents selected from the group consisting of Cl, Br, I, F, $NH_2$, —NH—(lower alkyl), —N(lower alkyl)$_2$, $CO_2H$, —$CO_2$—(lower alkyl), lower alkoxy, $NO_2$, $CF_3$, lower alkylthio or OH;

$R^2$, $R^3$, $R^4$, $R^5$ and $R^6$ are each independently selected from the group consisting of H, lower alkyl, lower alkoxy, Cl, Br, I and F; and $R^7$ and $R^8$ are independently selected from the group consisting of H and lower alkyl;

WHICH COMPRISES treating the acylanilide of the Formula III

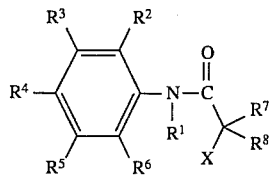

III wherein $R^1$, $R^2$, $R^3$, $R^4$, $R^5$, $R^6$, $R^7$ and $R^8$ are as defined hereinabove; and X is Cl, Br, I, p-toluenesulfonyloxy, trifluoromethyl sulfonyloxy or methylsulfonyloxy;

WITH A MIXTURE OF ammonium carbamate and aqueous ammonia solution, at a temperature from 40° to 80° C.

2. The process according to claim 1 wherein the temperature is from 55° to 70° C.

3. The process according to claim 1 for the preparation of a compound of the Formula Ia, tocainide:

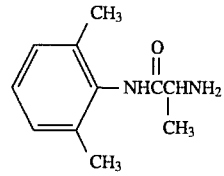

Ia which comprises treating the acylanilide of the Formula IIIa

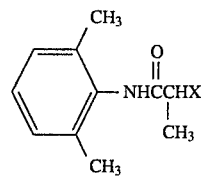

IIIa wherein X is Cl, Br or I;

with a mixture of ammonium carbamate and aqueous ammonia solution, at a temperature from 40° to 80° C.

4. The process according to claim 3 wherein the temperature is from 55° to 70° C.

* * * * *